(12) United States Patent
Chiu et al.

(10) Patent No.: US 9,797,840 B2
(45) Date of Patent: Oct. 24, 2017

(54) HIGHLY FLUORESCENT POLYMER NANOPARTICLE

(71) Applicant: University of Washington through its Center for Commercialization, Seattle, WA (US)

(72) Inventors: Daniel T. Chiu, Seattle, WA (US);
Changfeng Wu, Seattle, WA (US);
Fangmao Ye, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 13/687,813

(22) Filed: Nov. 28, 2012

(65) Prior Publication Data
US 2013/0266957 A1    Oct. 10, 2013

Related U.S. Application Data

(60) Provisional application No. 61/563,947, filed on Nov. 28, 2011.

(51) Int. Cl.
| | | |
|---|---|---|
| *B82Y 15/00* | (2011.01) | |
| *G01N 21/64* | (2006.01) | |
| *G01N 33/58* | (2006.01) | |

(52) U.S. Cl.
CPC .......... *G01N 21/6486* (2013.01); *B82Y 15/00* (2013.01); *G01N 33/588* (2013.01); *Y10T 428/2982* (2015.01)

(58) Field of Classification Search
CPC   B82Y 5/00; C12Q 2563/125; A61K 49/0093; A61K 49/0021; A61K 49/1875; A61K 49/0423; A61K 49/1824; A61K 49/0428

USPC .................................................. 436/518, 525
See application file for complete search history.

(56) References Cited

U.S. PATENT DOCUMENTS

| | | |
|---|---|---|
| 4,946,778 A | 8/1990 | Ladner et al. |
| 6,417,402 B1 | 7/2002 | Das et al. |
| 7,432,298 B2 | 10/2008 | Lam et al. |
| 7,462,325 B2 | 12/2008 | Hancock et al. |
| 7,521,232 B2 | 4/2009 | Moon |
| 8,367,042 B2 | 2/2013 | Kim et al. |
| 9,382,473 B2 | 7/2016 | Chiu et al. |
| 2004/0018379 A1* | 1/2004 | Kinlen .......................... 428/690 |

(Continued)

FOREIGN PATENT DOCUMENTS

| | | |
|---|---|---|
| CN | 1541136 A | 10/2004 |
| WO | WO 2007/027159 A1 | 3/2007 |

(Continued)

OTHER PUBLICATIONS

Pecher et al., "Nanoparticles of Conjugated Polymers", Chem. Rev., vol. 110, pp. 6260-6279, published Aug. 4, 2010.*

(Continued)

*Primary Examiner* — Mark Shibuya
*Assistant Examiner* — Nam Nguyen
(74) *Attorney, Agent, or Firm* — Wilson Sonsini Goodrich & Rosati (57) ABSTRACT

Fluorescent nanoparticles are provided. The nanoparticles are formed from poly[2-methoxy-5-(2-ethylhexyloxy)-1,4-(1-cyanovinylene-1,4-phenylene)]. Also provided are methods for imaging a target to which the nanoparticles are bound.

6 Claims, 6 Drawing Sheets

(56) References Cited

U.S. PATENT DOCUMENTS

| | | | |
|---|---|---|---|
| 2004/0131886 | A1 | 7/2004 | Marrocco et al. |
| 2005/0019265 | A1 | 1/2005 | Hammer et al. |
| 2005/0171289 | A1 | 8/2005 | Kataoka et al. |
| 2005/0255044 | A1 | 11/2005 | Lomnes et al. |
| 2006/0127929 | A1 | 6/2006 | Swager et al. |
| 2007/0031490 | A1 | 2/2007 | Loebenberg et al. |
| 2007/0224345 | A1 | 9/2007 | Metz et al. |
| 2008/0081192 | A1 | 4/2008 | Goh et al. |
| 2008/0085566 | A1 | 4/2008 | Swager et al. |
| 2008/0178763 | A1 | 7/2008 | Schwartz et al. |
| 2008/0199700 | A1 | 8/2008 | Anderson et al. |
| 2008/0242806 | A1* | 10/2008 | Chen .................. C08J 3/03 525/450 |
| 2009/0075295 | A1 | 3/2009 | Lindsey |
| 2009/0130665 | A1 | 5/2009 | Sleiman et al. |
| 2009/0220434 | A1* | 9/2009 | Sharma ................ 424/9.323 |
| 2010/0016472 | A1 | 1/2010 | Wang et al. |
| 2010/0098902 | A1 | 4/2010 | Kotov et al. |
| 2010/0290999 | A1* | 11/2010 | Kim et al. ............... 424/9.6 |
| 2011/0159605 | A1 | 6/2011 | Whitten et al. |
| 2011/0278503 | A1 | 11/2011 | Janczewski et al. |
| 2011/0278536 | A1 | 11/2011 | Walker et al. |
| 2012/0015190 | A1 | 1/2012 | Goh et al. |
| 2012/0175571 | A1 | 7/2012 | Sarkar |
| 2012/0282632 | A1 | 11/2012 | Chiu et al. |
| 2013/0234067 | A1 | 9/2013 | Chiu et al. |
| 2013/0234068 | A1 | 9/2013 | Chiu et al. |
| 2013/0266957 | A1 | 10/2013 | Chiu et al. |
| 2014/0302516 | A1 | 10/2014 | Chiu et al. |
| 2014/0350183 | A1 | 11/2014 | Chiu et al. |
| 2015/0037259 | A1 | 2/2015 | Chiu et al. |
| 2016/0018395 | A1 | 1/2016 | Chiu et al. |
| 2016/0161475 | A1 | 6/2016 | Chiu et al. |
| 2016/0341737 | A1 | 11/2016 | Chiu et al. |

FOREIGN PATENT DOCUMENTS

| | | |
|---|---|---|
| WO | WO 2007/095506 A1 | 8/2007 |
| WO | WO 2008/063378 A2 | 5/2008 |
| WO | WO 2009/051560 A1 | 4/2009 |
| WO | WO 2009/107859 A2 | 9/2009 |
| WO | WO 2010/006753 A2 | 1/2010 |
| WO | WO 2011/057295 A2 | 5/2011 |
| WO | WO 2013/101902 A2 | 7/2013 |

OTHER PUBLICATIONS

Greenham et al., "Efficient light-emitting diodes based on polymers with high electron affinities", Nature, vol. 365, pp. 628-630, published Oct. 14, 1993, print retrieved on Oct. 10, 2016.*

Wu et al., "Ultrabright and Bioorthogonal Labeling of Cellular Targets Using Semiconducting Polymer Dots and Click Chemistry", Angew. Chem. Int. Ed., vol. 49, pp. 9436-9440, published Oct. 26, 2010.*

Greenham et al. "Meansurement of absolute photoluminescence quantum efficiencies in conjugated polymers", Chemical Physics Letters, vol. 241, pp. 89-96, published 1995.*

Wu, C., et al., "Bioconjugation of Ultrabright Semiconducting Polymer Dots for Specific Cellular Targeting," Journal of the American Chemical Society 132(43):15410-15417, Nov. 2010.

Achari, et al. 1.67-A X-ray structure of the B2 immunoglobulin-binding domain of streptococcal protein G and comparison to the NMR structure of the B1 domain. Biochemistry. Nov. 3, 1992;31(43):10449-57.

Akerstrom, et al. A physicochemical study of protein G, a molecule with unique immunoglobulin G-binding properties. J Biol Chem. Aug. 5, 1986;261(22):10240-7.

Bird, et al. Single-chain antigen-binding proteins. Science. Oct. 21, 1988;242(4877):423-6.

Green. Avidin and streptavidin. Methods Enzymol. Wilchek and Bayer. New York, Academic Press, Inc. 1990;184:51-67.

Dube, et al. Probing mucin-type O-linked glycosylation in living animals. Proc Natl Acad Sci U S A. Mar. 28, 2006;103(13):4819-24. Epub Mar. 20, 2006.

Hermanson. Bioconjugate techniques, Academic Press, San Diego, 1996; Ch 13, 570-591.

International search report and written opinion dated Aug. 22, 2014 for PCT/US2014/028846.

Abbel, et al. Multicolour self-assembled particles of fluorene-based bolaamphiphiles. Chem Commun (Camb). Apr. 7, 2009;(13):1697-9. doi: 10.1039/b822943k. Epub Feb. 17, 2009.

Agard, et al. A comparative study of bioorthogonal reactions with azides. ACS Chem Biol. Nov. 21, 2006;1(10):644-8.

Alivistatos, et al. Quantum dots as cellular probes. Annu Rev Biomed Eng. 2005;7:55-76.

Ausborn, et al. The protective effect of free and membrane-bound cryoprotectants during freezing and freeze-drying of liposomes. Journal of Controlled Release. 1994; 30:105-116.

Baler, et al. Fluorescent conjugated polymer nanoparticles by polymerization in miniemulsion. J Am Chem Soc. Oct. 14, 2009;131(40):14267-73. doi: 10.1021/ja905077c.

Berlier, et al. Quantitative comparison of long-wavelength Alexa Fluor dyes to Cy dyes: fluorescence of the dyes and their bioconjugates. J Histochem Cytochem. Dec. 2003;51(12):1699-712.

Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.

Best. Click chemistry and bioorthogonal reactions: unprecedented selectivity in the labeling of biological molecules. Biochemistry. Jul. 21, 2009;48(28):6571-84. doi: 10.1021/bi9007726.

Breidenbach, et al. Targeted metabolic labeling of yeast N-glycans with unnatural sugars. Proc Natl Acad Sci U S A. Mar. 2, 2010;107(9):3988-93. doi: 10.1073/pnas.0911247107. Epub Feb. 8, 2010.

Bruchez, et al. Semiconductor nanocrystals as fluorescent biological labels. Science. Sep. 25, 1998;281(5385):2013-6.

Caruso. Nanoengineering of Particle Surfaces. Adv. Mater. 2001; 13:11-22.

Chalfie, et al. Green fluorescent protein as a marker for gene expression. Science. Feb. 11, 1994;263(5148):802-5.

Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.

Chan, et al. Development of ultrabright semiconducting polymer dots for ratiometric pH sensing. Anal Chem. Feb. 15, 2011;83(4):1448-55. doi: 10.1021/ac103140x. Epub Jan. 18, 2011.

Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.

Chan, et al. Quantum dot bioconjugates for ultrasensitive nonisotopic detection. Science. Sep. 25, 1998;281(5385):2016-8.

Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.

Chen, et al. Highly sensitive biological and chemical sensors based on reversible fluorescence quenching in a conjugated polymer. Proc Natl Acad Sci U S A. Oct. 26, 1999;96(22):12287-92.

Choi, et al. Design considerations for tumour-targeted nanoparticles. Nat Nanotechnol. Jan. 2010;5(1):42-7. doi: 10.1038/nnano.2009.314. Epub Nov. 1, 2009.

Choi, et al. Renal clearance of quantum dots. Nat Biotechnol. Oct. 2007;25(10):1165-70. Epub Sep. 23, 2007.

Clafton, et al. Chemical defects in the highly fluorescent conjugated polymer dots. Langmuir. Dec. 7, 2010;26(23):17785-9. doi: 10.1021/la103063p. Epub Nov. 11, 2010.

Collini, et al. Coherent intrachain energy migration in a conjugated polymer at room temperature. Science. Jan. 16, 2009;323(5912):369-73. doi: 10.1126/science.1164016.

Derfus, et al. Probing the Cytotoxicity of Semiconductor Quantum Dots. Nano Letters. 2004; 4(1):11-18.

(56) References Cited

OTHER PUBLICATIONS

Dieterich, et al. Selective identification of newly synthesized proteins in mammalian cells using bioorthogonal noncanonical amino acid tagging (BONCAT). Proc Natl Acad Sci U S A. Jun. 20, 2006;103(25):9482-7. Epub Jun. 12, 2006.
European search report and opinion dated Mar. 19, 2014 for EP Application No. 11835019.8.
European search report and opinion dated Sep. 18, 2013 for EP Application No. 10829306.9.
Fan, et al. Beyond superquenching: hyper-efficient energy transfer from conjugated polymers to gold nanoparticles. Proc Natl Acad Sci U S A. May 27, 2003;100(11):6297-301. Epub May 15, 2003.
Fernandez-Suarez, et al. Fluorescent probes for super-resolution imaging in living cells. Nat Rev Mol Cell Biol. Dec. 2008;9(12):929-43. doi: 10.1038/nrm2531. Epub Nov. 12, 2008.
Fernando, et al. Mechanism of cellular uptake of highly fluorescent conjugated polymer nanoparticles. Biomacromolecules. Oct. 11, 2010;11(10):2675-82. doi: 10.1021/bm1007103.
Friend, et al. Electroluminescence in conjugated polymers. Nature. 1999; 397:121-128.
Giepmans, et al. The fluorescent toolbox for assessing protein location and function. Science. Apr. 14, 2006;312(5771):217-24.
Gunes, et al. Conjugated polymer-based organic solar cells. Chem Rev. Apr. 2007;107(4):1324-38.
Han, et al. Development of a bioorthogonal and highly efficient conjugation method for quantum dots using tetrazine-norbornene cycloaddition. J Am Chem Soc. Jun. 16, 2010;132(23):7838-9. doi: 10.1021/ja101677r.
Hashim, et al. Luminescent quantum-dot-sized conjugated polymer nanoparticles—nanoparticle formation in miniemulsion system. Journal of Materials Chemistry. 2011; 21: 1797-1803.
Hermanson. Bioconjugate techniques, Academic Press, San Diego, 1996.
Hou, et al. Novel red-emitting fluorene-based copolymers. Journal of Materials Chemistry. 2002; 12:2887-2892.
Hou, et al. Synthesis and electroluminescent properties of high-efficiency saturated red emitter based on copolymers from fluorene and 4,7- di(4-hexylthien-2-yl)-2,1,3-benzothiadiazole, Macromolecules. 2004; 37:6299-6305.
Howarth, et al. Monovalent, reduced-size quantum dots for imaging receptors on living cells. Nat Methods. May 2008;5(5):397-9. doi: 10.1038/nmeth.1206. Epub Apr. 20, 2008.
Howes, et al. Colloidal and optical stability of PEG-capped and phospholipid-encapsulated semiconducting polymer nanospheres in different aqueous media. Photochem Photobiol Sci. Aug. 2010;9(8):1159-66. doi: 10.1039/c0pp00106f. Epub Jun. 29, 2010.
Howes, et al. Magnetic conjugated polymer nanoparticles as bimodal imaging agents. J Am Chem Soc. Jul. 21, 2010;132(28):9833-42. doi: 10.1021/ja1031634.
Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.
International preliminary report on patentability dated Apr. 23, 2013 for PCT/US2011/056768.
International search report and written opinion dated Mar. 27, 2013 for PCT/US2012/071767.
International search report and written opinion dated Apr. 9, 2013 for PCT/US2013/024300.
International search report and written opinion dated Jun. 26, 2012 for PCT/US2011/056768.
International search report and written opinion dated Jul. 28, 2011 for PCT/US2010/056079.
Jin, et al. Generation of functionalized and robust semiconducting polymer dots with polyelectrolytes. Chem Commun (Camb). Mar. 28, 2012;48(26):3161-3. doi: 10.1039/c2cc17703j. Epub Feb. 20, 2012.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.
Jin, et al. Silica Nanoparticles with Continuously Tunable Sizes: Synthesis and Size Effects on Cellular Imaging. Chem. Mater. 2008, 20:4411-4419.
Johnston, et al. Layer-by-layer engineered capsules and their applications. Curr. Opin. Colloid Interface Sci. 2006; 11:203-209.
Kaeser, et al. Fluorescent nanoparticles based on self-assembled pi-conjugated systems. Adv Mater. Jul. 27, 2010;22(28):2985-97. doi: 10.1002/adma.201000427.
Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.
Kolb, et al. Click Chemistry: Diverse Chemical Function from a Few Good Reactions. w Chem Int Ed Engl. Jun. 1, 2001;40(11):2004-2021.
Kolb, et al. The growing impact of click chemistry on drug discovery. Drug Discov Today. Dec. 15, 2003;8(24):1128-37.
Kumar, et al. Photon antibunching from oriented semiconducting polymer nanostructures. J Am Chem Soc. Mar. 24, 2004;126(11):3376-7.
Laughlin, et al. Imaging the glycome. Proc Natl Acad Sci U S A. Jan. 6, 2009;106(1):12-7. doi: 10.1073/pnas.0811481106. Epub Dec. 22, 2008.
Lee, et al. Recent advances in fluorescent and colorimetric conjugated polymer-based biosensors. Analyst. Sep. 2010;135(9):2179-89. doi: 10.1039/c0an00239a. Epub Jun. 11, 2010.
Li, et al. Polymer encapsulated conjugated polymer nanoparticles for fluorescence bioimaging. Journal of Materials Chemistry 2012; 22:1257-1264.
McCafferty, et al. Phage antibodies: filamentous phage displaying antibody variable domains. Nature. Dec. 6, 1990;348(6301):552-4.
Michalet, et al. Quantum dots for live cells, in vivo imaging, and diagnostics. Science. Jan. 28, 2005;307(5709):538-44.
Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.
Moon, et al. Live-cell-permeable poly(p-phenylene ethynylene). Angew Chem Int Ed Engl. 2007;46(43):8223-5.
Moses, et al. The growing applications of click chemistry. Chem Soc Rev. Aug. 2007;36(8):1249-62. Epub May 3, 2007.
Nirmal, et al. Fluorescence intermittency in single cadmium selenide nanocrystals. Nature. 1996; 383:802-804. doi:10.1038/383802a0.
Palacios, et al. Charging and discharging of single conjugated-polymer nanoparticles. Nat Mater. Sep. 2007;6(9):680-5. Epub Jul. 22, 2007.
Pecher, et al. Nanoparticles of conjugated polymers. Chem Rev. Oct. 13, 2010;110(10):6260-79. doi: 10.1021/cr100132y.
Pepperkok, et al. High-throughput fluorescence microscopy for systems biology. Nat Rev Mol Cell Biol. Sep. 2006;7(9):690-6. Epub Jul. 19, 2006.
Poon, et al. Controlling in vivo stability and biodistribution in electrostatically assembled nanoparticles for systemic delivery. Nano Lett. May 11, 2011;11(5):2096-103. doi: 10.1021/nl200636r. Epub Apr. 27, 2011.
Poon, et al. Layer-by-layer nanoparticles with a pH-sheddable layer for in vivo targeting of tumor hypoxia. ACS Nano. Jun. 28, 2011;5(6):4284-92. doi: 10.1021/nn200876f Epub Apr. 29, 2011.
Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.
Prescher, et al. Chemical remodelling of cell surfaces in living animals. Nature. Aug. 19, 2004;430(7002):873-7.
Prescher, et al. Chemistry in living systems. Nat Chem Biol. Jun. 2005;1(1):13-21.
Pu, et al. Fluorescent conjugated polyelectroltyes for bioimaging. Advanced Functional Materials. 2011; 21:3408-3423.
Pu, et al. Fluorescent single-molecular core-shell nanospheres of hyperbranched conjugated polyelectrolyte for live-cell imaging. Chem. Mater. 2009;21:3816-3822.
Que, et al. Metals in neurobiology: probing their chemistry and biology with molecular imaging. Chem Rev. May 2008;108(5):1517-49. doi: 10.1021/cr078203u. Epub Apr. 22, 2008.

(56) References Cited

OTHER PUBLICATIONS

Rahim, et al. Conjugated Polymer Nanoparticles for Two-Photon Imaging of Endothelial Cells in a Tissue Model. Adv. Mater. 2009; 21(34):3492-3496.

Resch-Genger, et al. Quantum dots versus organic dyes as fluorescent labels. Nat Methods. Sep. 2008;5(9):763-75. doi: 10.1038/nmeth.1248.

Sadtler, et al. Selective facet reactivity during cation exchange in cadmium sulfide nanorods. J Am Chem Soc. Apr. 15, 2009;131(14):5285-93. doi: 10.1021/ja809854q.

Sigma Aldrich. Product Information Triton X-1 00. Apr. 21, 1999. Retrieved at http://www.sigmaaldrich.com/content!dam/ sigmaaldrich/docs/Sigma/Product_lnformation_Sheet/1 /t8532pis. pdf on Mar. 14, 2014.

Sletten, et al. Bioorthogonal chemistry: fishing for selectivity in a sea of functionality. Angew Chem Int Ed Engl. 2009;48(38):6974-98. doi: 10.1002/anie.200900942.

Smith, et al. Investigating lyophilization of lipid nanocapsules with fluorescence correlation spectroscopy. Langmuir. Jun. 15, 2010;26(12):10218-22. doi: 10.1021/la1003808.

Speers, et al. Activity-based protein profiling in vivo using a copper(i)-catalyzed azide-alkyne [3 + 2] cycloaddition. J Am Chem Soc. Apr. 23, 2003;125(16):4686-7.

Szymanski, et al. Single molecule nanoparticles of the conjugated polymer MEH-PPV, preparation and characterization by near-field scanning optical microscopy. J Phys Chem B. May 12, 2005;109(18):8543-6.

Thomas, et al. Chemical sensors based on amplifying fluorescent conjugated polymers. Chem Rev. Apr. 2007;107(4):1339-86. Epub Mar. 27, 2007.

Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.

Tsien. The green fluorescent protein. Annu Rev Biochem. 1998;67:509-44.

Tuncel, et al. Conjugated polymer nanoparticles. Nanoscale. Apr. 2010;2(4):484-94. doi: 10.1039/b9nr00374f. Epub Mar. 6, 2010.

Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.

Wang, et al. Bioconjugation by copper(I)-catalyzed azide-alkyne [3 + 2] cycloaddition. J Am Chem Soc. Mar. 19, 2003;125(11):3192-3.

Wang, et al. Non-blinking semiconductor nanocrystals. Nature. Jun. 4, 2009;459(7247):686-9. doi: 10.1038/nature08072.

Wang, et al. Watching silica nanoparticles glow in the biological world. Anal. Chem. 2006;78(3):646-654.

Wu, et al. Conjugated polymer dots for multiphoton fluorescence imaging. J Am Chem Soc. Oct. 31, 2007;129(43):12904-5. Epub Oct. 6, 2007.

Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.

Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.

Wu, et al. Energy transfer mediated fluorescence from blended conjugated polymer nanoparticles. J Phys Chem B. Jul. 27, 2006;110(29):14148-54.

Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.

Wu, et al. Immunofluorescent labeling of cancer marker Her2 and other cellular targets with semiconductor quantum dots. Nat Biotechnol. Jan. 2003;21(1):41-6. Epub Dec. 2, 2002.

Wu, et al. Multicolor conjugated polymer dots for biological fluorescence imaging. ACS Nano. Nov. 25, 2008;2(11):2415-23. doi: 10.1021/nn800590n.

Wu, et al. Preparation and encapsulation of highly fluorescent conjugated polymer nanoparticles. Langmuir. Mar. 28, 2006;22(7):2956-60.

Wu, et al. Ratiometric single-nanoparticle oxygen sensors for biological imaging. Angew Chem Int Ed Engl. 2009;48(15):2741-5. doi: 10.1002/anie.200805894.

Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.

Wu. Fluorescent conjugated polymer dots for single molecule imaging and sensing application a Dissertation presented to the Graduate School of Clemson University. Dec. 1, 2008. pp. 1-182. http://etd.lib.clemson.edu/documents/1239895063/Wu_clemson_005D_10023.pdf.

Xie, et al. Luminescent CdSe-ZnSe quantum dots as selective Cu2+ probe. Spectrochimica Acta Part A. 2004; 60:2527-2530.

Xing, et al. Bioconjugated quantum dots for multiplexed and quantitative immunohistochemistry. Nat Protoc. 2007;2(5):1152-65.

Yang, et al. Deep-red electroluminescent polymers: Synthesis and characterization of new low-band-gap conjugated copolymers for light-emitting diodes and photovoltaic devices. Macromolecules 2005; 38:244-253.

Yao, et al. Blinking and nonradiant dark fraction of water-soluble quantum dots in aqueous solution. Proc Natl Acad Sci U S A. Oct. 4, 2005;102(40):14284-9. Epub Sep. 16, 2005.

Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.

Ye, et al. Ratiometric temperature sensing with semiconducting polymer dots. J Am Chem Soc. Jun. 1, 2011;133(21):8146-9. doi: 10.1021/ja202945g. Epub May 11, 2011.

Yu, et al. Nanoscale 3D tracking with conjugated polymer nanoparticles. J Am Chem Soc. Dec. 30, 2009;131(51):18410-4. doi: 10.1021/ja907228q.

Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.

Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.

Zheng. Detection of the cancer marker CD146 expression in melanoma cells with semiconductor quantum dot label (Abstract). J Biomed Nanotechnol. Aug. 2010;6(4):303-11.

Boyere, et al. Elaboration of drug nanocarriers based on a glucosamine labeled amphiphilic polymer. Polymer Chemistry. 2014; 5:3030-3037.

European search report and opinion dated Oct. 8, 2015 for EP Application No. 13743132.6.

Office action dated Feb. 2, 2016 for CN Application No. 20118006824.2.

Office action dated Feb. 4, 2015 for CN Application No. 20118006824.2.

Office action dated Apr. 28, 2014 for AU Application No. 2011317142.

Office action dated May 30, 2014 for CN Application No. 20118006824.2.

Office action dated Aug. 4, 2015 for CN Application No. 20118006824.2.

Office action dated Dec. 3, 2015 for JP Application No. 2013-535014.

Thivierge, et al. Brilliant BODIPY-fluorene Copolymers With Dispersed Absorption and Emission Maxima Macromolecules. May 24, 2011;44(10):4012-4015.

European search report and opinion dated Aug. 12, 2015 for EP Application No. 15175146.8.

(56) References Cited

OTHER PUBLICATIONS

Howes, et al. Synthesis, characterisation and intracellular imaging of PEG capped BEHP-PPV nanospheres. Chem Commun (Camb). May 14, 2009;(18):2490-2. doi: 10.1039/b903405f Epub Apr. 2, 2009.

Kietzke, et al. Novel approaches to polymer blends based on polymer nanoparticles. Nat Mater. Jun. 2003;2(6):408-12.

Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.

Wu, et al. Swelling-controlled polymer phase and fluorescence properties of polyfluorene nanoparticles. Langmuir. Jun. 3, 2008;24(11):5855-61. doi: 10.1021/la8000762. Epub May 7, 2008.

Australian examination report dated Apr. 8, 2016 for AU Application 2015204342.

European office action dated Mar. 2, 2016 for EP Application No. 11835019.8.

Huyal, et al., White emitting polyfluorene functionalized with azide hybridized on near-UV light emitting diode for high color rendering index, Optics Express , Jan. 21, 2008, 16(2):1115-24.

Meng, et al. Color tuning of polyfluorene emission with Bodipy monomers, Macromolecules 2009, 42:1995-2001.

Office action dated Feb. 11, 2016 for U.S. Appl. No. 13/865,942.

Office action dated Mar. 8, 2017 for AU Application No. 2015204342.

Office action dated Mar. 30, 2017 for U.S. Appl. No. 14/373,835.

Office action dated Mar. 31, 2016 for JP Application No. 2012-538915.

Office action dated Apr. 5, 2017 for EP Application No. 15175146.8.

Office action dated May 16, 2016 for U.S. Appl. No. 14/373,835.

Office action dated May 20, 2016 for EP Application No. 10829306.9.

Office action dated Sep. 29, 2016 for CN Application No. 201180060824.2.

Office action dated Dec. 29, 2016 for U.S. Appl. No. 13/865,942.

Office action dated Jan. 30, 2017 for AU Application No. 2012362466.

Office action dated Feb. 22, 2017 for U.S. Appl. No. 13/508,981.

Office action dated Mar. 1, 2017 for U.S. Appl. No. 14/366,863.

Office action dated Sep. 13, 2016 for U.S. Appl. No. 14/373,835.

Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.

Yao, et al., Fluorescent Nanoparticles Comprising Amphiphilic Rod-Coil Graft Copolymers, Macromolecules, 2008, 41:1438-43.

* cited by examiner

HIGHLY FLUORESCENT POLYMER NANOPARTICLE

CROSS-REFERENCE TO RELATED APPLICATION

This application claims the benefit of U.S. Patent Application No. 61/563,947, filed Nov. 28, 2011, the disclosure of which is hereby incorporated by reference in its entirety.

STATEMENT OF GOVERNMENT LICENSE RIGHTS

This invention was made with government support under R01NS052637 and R01GM085485, awarded by the National Institutes of Health, and CHE-0924320, awarded by the National Science Foundation. The government has certain rights in the invention.

BACKGROUND

Semiconducting polymer dots ("Pdots," used herein to describe a nanoscale polymer particle) possess large absorption cross-sections, high quantum yields, and fast emission rates. These optical properties make them well-suited for biological detection and imaging, high-speed single-particle tracking, and various biosensing platforms. Recently Pdot-bioconjugates have been developed and their applications in specific cellular imaging, bioorthogonal labeling, and in vivo tumor targeting, have been demonstrated. Successful bioconjugation opens up a new and practical way to employ the highly fluorescent and non-toxic Pdot-bioconjugates for a wide variety of biological applications.

Despite the field's progress, there is still a great need to explore new polymer species that form highly fluorescent Pdots, especially ones that complement the absorption and emission properties of currently available Pdots.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a nanoparticle is provided. In one embodiment, the nanoparticle comprises poly[2-methoxy-5-(2-ethylhexyloxy)-1,4-(1-cyanovinylene-1,4-phenylene)], wherein the nanoparticle has at least one critical dimension of 1 nm to 1000 nm. In some instances, the nanoparticles disclosed herein are referred to as Pdots.

In another aspect, a method is provided for imaging a target. In one embodiment, the method includes the steps of:
(a) binding a nanoparticle having a binding moiety to a target;
(b) illuminating the nanoparticle with electromagnetic radiation sufficient to produce a fluorescence signal; and
(c) detecting the fluorescence signal.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Fluorescent nanoparticles are provided. The nanoparticles are formed from poly[2-methoxy-5-(2-ethylhexyloxy)-1,4-(1-cyanovinylene-1,4-phenylene)]. Also provided are methods for imaging a target to which the nanoparticles are bound.

In one aspect, a nanoparticle is provided. In one embodiment, the nanoparticle comprises poly[2-methoxy-5-(2-ethylhexyloxy)-1,4-(1-cyanovinylene-1,4-phenylene)], wherein the nanoparticle has at least one critical dimension of 1 nm to 1000 nm. In some instances, the nanoparticles disclosed herein are referred to as Pdots.

The provided nanoparticles are optimized for use as photoluminescent reporters that can be attached to a target as part of an imaging scheme. Two essential aspects of the nanoparticles (when used for imaging) are (1) the nanoparticles should only minimally disrupt the functions of the target; and (2) the nanoparticles should be easily detectable using photoluminescence. Unfortunately, these two design aspects are typically mutually exclusive because smaller particles that incorporate photoluminescent material will produce a smaller overall light flux than a larger particle of the same material. Additionally, as particles are reduced further on the size scale towards the 1-20 nm range, additional effects further limit the photoluminescent activity, such as self-quenching.

In order to provide nanoparticles that are sufficiently small yet retain strong photoluminescence, the inventors synthesized nanoparticles of poly[2-methoxy-5-(2-ethylhexyloxy)-1,4-(1-cyanovinylene-1,4-phenylene)], referred to herein as "CN-PPV." While cyano-polyphenylene vinylene polymers are know for their light-emitting properties, it was discovered through experimentation that poly[2- methoxy-5-(2-ethylhexyloxy)-1,4-(1-cyanovinylene-1,4-phenylene)] could be formed into sufficiently small particles that, in turn, exhibited sufficient photoluminescence for bioimaging applications.

The nano-scale size of the nanoparticle is essential in order to bypass issues presented by large particle sizes. For example, when attaching the nanoparticles to a target (e.g., a biomolecules) for photoluminescence imaging, relatively large particles may alter the biological function and transport of the attached biomolecules. Conversely, relatively small nanoparticles, such as those disclosed herein, minimally disrupt the functions of such biomolecules. Small nanoparticles are particularly useful for subcellular imaging because large-sized particles may cause problems such as poor mass transfer and tissue penetration as well as non-specific adsorption.

As used herein, a relatively "large" nanoparticle has a critical dimension (e.g., diameter) greater than about 20 nm to 30 nm. A "small" nanoparticle is smaller than about 20 nm to 30 nm.

The size of the nanoparticles provided herein are defined in terms of a "critical dimension," which refers to the smallest dimension of the nanoparticle (i.e., the dimension that gives the particle nanoscopic size). Many nanoparticles are roughly spherical in shape, which results in the critical dimension being the radius or diameter of the spherical particle. The hydrodynamic radius or diameter can also be used to define the nanoparticle size. The critical dimension of non-spherical nanoparticles is determined by the specific shape at issue. While typical nanoparticles, such as nanospheres and nanocubes, are completely nanoscopic in size, not every dimension of the nanoparticle needs to be at the nanoscale. For example, a nano-cylinder may have a diameter on the nano-scale but a length on the micro-scale.

The possible shape of the nanoparticle is essentially unlimited. However, in certain embodiments, the shape is selected from a sphere, a cylinder, an ellipsoid, a polyhedron, a prism, a rod, and a wire. The shape of the nanoparticle may contribute to the detection properties, as will be appreciated by those of skill in the art (e.g., nano-rods may have different optical properties than nano-spheres).

In one embodiment, the critical dimension is 30 nm or less. In one embodiment, the critical dimension is 25 nm or less. In one embodiment, the critical dimension is 20 nm or less. In one embodiment, the critical dimension is 15 nm or less. In another embodiment, the critical dimension is 10 nm or less. In yet another embodiment, the critical dimension is 5 nm or less.

In one embodiment, the nanoparticle consists essentially of CN-PPV. In another embodiment, the nanoparticle includes CN-PPV and at least one other material. For example, the CN-PPV can be mixed with a copolymer or other material that provides an additional functionality that the CN-PPV does not. A representative embodiment of a copolymer is described in further detail in the EXAMPLE below. Any copolymer or other material known to those of skill in the art can be used, as long as the essential aspects of the nanoparticle described herein are maintained (e.g., size, photoluminescence, etc.).

In certain embodiments, the nanoparticle has a fluorescence emission peak in the range of about 590 nm to about 620 nm. It will be appreciated, however, that many factors can shift the fluorescence emission characteristics of the CN-PPV, including surface functionalization of the nanoparticle, the presence of a copolymer, solvent effect, and binding effects (if the nanoparticle is attached to a target).

The superior fluorescence of the nanoparticles arises from CN-PPV, which exhibits a large absorption cross-section, high quantum yield, and a fast emission rate. In certain embodiments, the quantum yield of the nanoparticle is 20% or greater. In certain embodiments, the emission rate is from 0.1 nanoseconds to 50 nanoseconds.

In certain embodiments, the surface of the nanoparticle has a functional group. The functional group may be attached to the CN-PPV itself (e.g., as a copolymer or pendant group). Alternatively, the functional group may be a part of a copolymer that is then combined with CN-PPV to form the nanoparticle.

The functional group can be any moiety having a functionality to react or bind to a moiety external to the nanoparticle. For example, a functional group may be a moiety configured to bind to a target (i.e., the functional group is a binding moiety, as described elsewhere herein), or the functional group may be a group capable of reacting with another molecule to form a binding moiety.

In one embodiment, the functional group is a carboxylic acid functionality. As noted in the EXAMPLE below, a carboxylic acid moiety can be used to conjugate the nanoparticle to streptavidin.

In certain embodiments, the nanoparticle further comprises a binding moiety configured to bind to a target. The binding moiety may be attached to the CN-PPV itself (e.g., as a copolymer or pendant group). Alternatively, the binding moiety may be a part of a copolymer that is then combined with CN-PPV to form the nanoparticle.

The target is an analyte in solution with the nanoparticle. In embodiments where the nanoparticle includes a capture moiety, the capture moiety binds to the target in solution and the fluorescence of the nanoparticle can be used to report the presence of the target. Representative targets include an antibody, an antigen, a cell, a nucleic acid, an enzyme, a substrate for an enzyme, a protein, a lipid, a carbohydrate, or other biomarker.

Capture Moieties and Target Moieties

As used herein, the term "target" refers to a molecule or composition that is to be identified using the provided nanoparticle. In certain embodiments, the target is not itself detectable using the same photoluminescence techniques used to detect the nanoparticle.

In certain embodiments, the target is a diagnostic target that is indicative of a disease or condition, an indicator of exposure to a toxin, or other biomolecule.

In one embodiment, the target is a biomarker. Biomarkers can be protein, lipid, carbohydrate, or nucleic acid in nature. For each, the binding moiety has affinity for the target.

Examples of diseases or conditions that may be detected are endocrine, cardiac, and infectious diseases or conditions, and cancer. Suitable biomarkers for each of these are known to those skilled in the art. The scope of the invention also includes the detection of a target that is a protein expressed by mammalian or bacterial cells including cells engineered by recombinant techniques, or the detection of mammalian cells, viruses, or bacteria themselves, as is necessary for the assessment of clinical disease including conditions involving the fetus, and for food safety, or assessment of environmental conditions.

Other representative cells useful as a target include spores and single-celled organisms (e.g., parasites).

In certain embodiments, the target is an analyte indicative of the presence of a disease or condition, as will be described in more detail below. Representative diseases include infectious diseases such as human immunodeficiency virus (HIV), malaria, dengue, salmonella, rickettsia, influenza, chlamydia, and measles. In a representative embodiment, the infectious disease is present in a subject, and the presence of the infectious disease within the subject body produces antibodies or other biological markers that indicate the presence of the infectious disease in the body. Any of these analytes (antibodies or other biological markers) are targets advantageously detected in the present invention.

The target can be any protein or nucleic acid related to a disease.

In one embodiment, the target is an antibody and the binding moiety is an antigen. In one embodiment, the target is an antigen and the binding moiety is an antibody. In one embodiment, the target is a nucleic acid oligomer (RNA or DNA) and the binding moiety is a complementary nucleic acid oligomer. In one embodiment, the target is a nucleic acid oligomer (an RNA or a DNA) and the binding moiety is a protein. In one embodiment, the target is a protein and the binding moiety is a nucleic acid oligomer (RNA or DNA). In one embodiment, the target is an enzyme and the binding moiety is a substrate. In one embodiment, the target is an enzyme substrate and the binding moiety is an enzyme.

A binding moiety and a target form a binding pair. Each has an affinity toward the other (e.g., antigen and antibody). Each of the binding moiety and the target can be a variety of different molecules, including peptides, proteins, poly- or oligosaccharides, glycoproteins, lipids and lipoproteins, and nucleic acids, as well as synthetic organic or inorganic molecules having a defined bioactivity, such as an antibiotic or anti-inflammatory agent, that binds to a target site, such as a cell membrane receptor. Exemplary proteins include antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Exemplary oligonucleotides include DNA (genomic or cDNA), RNA, antisense, ribozymes, and external guide sequences for RNAase P, and can range in size from short oligonucleotide primers up to entire genes.

In one embodiment, the binding moiety is an antibody and the target is an antigen. In another embodiment, both the binding moiety and the target are protein. In another embodiment, the binding moiety is a nucleic acid (DNA or RNA) and the target is a complementary nucleic acid (DNA or RNA). In another embodiment, the target is a nucleic acid (DNA or RNA) and the binding moiety is a protein. In another embodiment, the binding moiety is a cell membrane receptor and the target is a ligand. In another embodiment, the binding moiety is an enzyme and the target is a substrate. In another embodiment, the binding moiety is biotin, or a biotin derivative, and the target is streptavidin or avidin conjugate of a target. In another embodiment, the binding moiety is an avidin (e.g., streptavidin) and the target is a biotinylated material effective for binding the target.

Among the proteins, streptavidin is particularly useful as a model for other binding moiety-target binding pair systems described herein, and also a component useful in many indirect separations and diagnostic technologies, which use the very strong association of the streptavidin-biotin affinity complex. (Wilchek and Bayer, *Avidin-Biotin Technology*, New York, Academic Press, Inc., 1990; and Green, *Meth. Enzymol.* 184:51-67. Protein G, a protein that binds IgG antibodies (Achari et al., *Biochemistry* 31:10449-10457, 1992, and Akerstrom and Bjorck, *J. Biol. Chem.* 261:10240-10247, 1986) is also useful as a model system. Representative immunoaffinity molecules include engineered single chain Fv antibody (Bird et al., *Science* 242:423-426, 1988 and U.S. Pat. No. 4,946,778, to Ladner et al., incorporated herein by reference, Fab, Fab', and monoclonal or polyclonal antibodies.

As used herein, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is a protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin. The term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

In another aspect, a method is provided for imaging a target. In one embodiment, the method includes the steps of:

(a) binding a nanoparticle having a binding moiety to a target;

(b) illuminating the nanoparticle with electromagnetic radiation sufficient to produce a fluorescence signal; and (c) detecting the fluorescence signal.

As described in detail above, the provided nanoparticles have both nanoscopic size and strong fluorescence. Therefore, the nanoparticles are attractive as imaging probes. In order to image a target, the nanoparticle is configured to have a binding moiety capable of binding to the target. This binding typically occurs in solution. Once the nanoparticle is bound to the target, the bound system is characterized using any photoluminescence technique known to those of skill in the art, including spectroscopy and microscopy. The fluorescence signal is improved by using a plurality of nanoparticles.

The nanoparticles provided herein can be formed using any technique known to those of skill in the art. In one embodiment, the nanoparticles are formed using nanoprecipitation, as described in more detail in the EXAMPLE below. In certain embodiments of the nanoprecipitation technique, ultrasound is used to disperse the particles in solution.

The following example is included for the purpose of illustrating, not limiting, the described embodiments.

EXAMPLE

In this example, we report a new Pdot species based on Poly[2-methoxy-5-(2-ethylhexyloxy)-1,4-(1-cyanovinylene-1,4-phenylene)] (CN-PPV). CN-PPV Pdots emit in the orange wavelength range, a region that currently lacks Pdots with high brightness. These CN-PPV Pdots, when formed by nanoprecipitation, are compact and small, with an average hydrodynamic diameter of ~10 nm. The CN-PPV dots exhibit bright orange fluorescence with a quantum yield of ~60%. Successful functionalization and bioconjugation produces CN-PPV Pdot-streptavidin probes that specifically label cell-surface markers and subcellular microtubule structures in mammalian cells. These results indicate the highly fluorescent CN-PPV Pdots are promising probes for cellular imaging and bioanalytical assays.

Figure 1A:
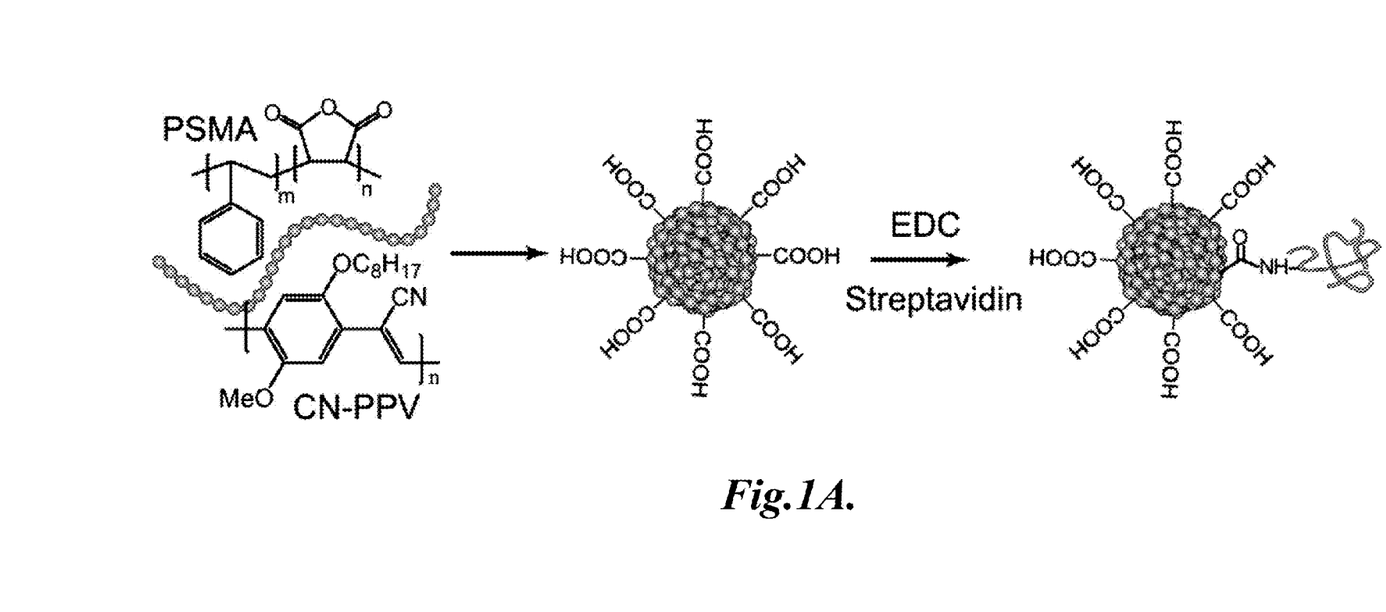
FIGS. 1A-1D. (1A) Surface functionalization of semiconducting polymer dots and subsequent streptavidin bioconjugation via EDC-catalyzed coupling. (1B) Hydrodynamic diameter of functionalized CN-PPV dots measured by DLS. (1C) Representative TEM image of functionalized CN-PPVdots. The scale bar represents 100 nm. (1D) Gel electrophoresis of Pdots with different surface functional groups.

The CN-PPV Pdot bioconjugates were prepared by nanoprecipitation. Briefly, we blended poly(styrene-co-maleic anhydride) (PSMA) with CN-PPV during Pdot formation, which resulted in carboxyl groups on the Pdot surface after the maleic anhydride groups were spontaneously hydrolyzed in aqueous solution (FIG. 1A). The CN-PPV-streptavidin bioconjugation step (electronic supplementary information; ESI) was then completed in 20 mM HEPES buffer containing 0.1% PEG in the presence of ethyl(dimethylaminopropyl) carbodiimide (EDC). The product was purified by column filtration and concentrated by membrane spin filtration.

Figure 1B:
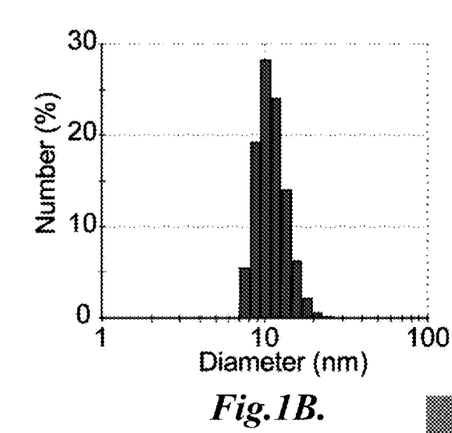
Figure 1C:
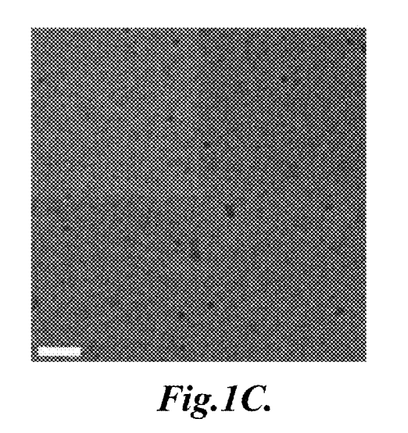

We characterized the size of the CN-PPV Pdots using dynamic light scattering (DLS, FIG. 1B) and transmission electron microscopy (TEM, FIG. 1C). The CN-PPV Pdots exhibited a hydrodynamic diameter of ~10 nm based on DLS measurements, which is consistent with the result from TEM. The carboxyl functionalization did not cause any noticeable change in the particle size. Under the same preparation conditions, the yellow-emitting carboxyl PFBT dots from our previous reports showed a hydrodynamic diameter larger than 15 nm. The size difference between the two Pdot species may be caused by differences in the rigidity of the polymer backbone and the molecular weight of the original polymer precursors. After streptavidin bioconjugation, the average hydrodynamic diameter of CN-PPV-streptavidin conjugates showed a slight increase of ~2 nm in diameter.

Figure 1D:
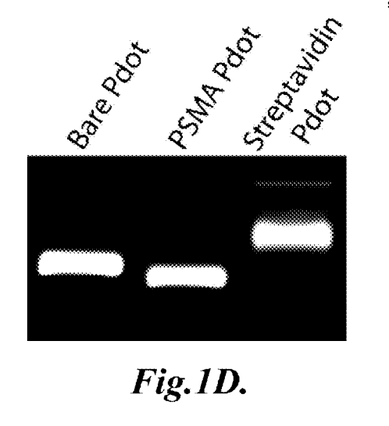

We performed gel electrophoresis to verify the formation of functional groups on the Pdot surface. FIG. 1D shows that the carboxyl-functionalized Pdot (PSMA-Pdot, middle column) exhibited an apparent increase in mobility compared to a bare Pdot (left column) in an agarose gel. The streptavidin-conjugated Pdot showed slower mobility than bare Pdot because of the decrease in negative surface charge together with the slight increase in the size of the Pdot-bioconjugates. These results suggest successful carboxyl functionalization of the Pdots as well as the surface bioconjugation with streptavidin.

Figure 2A:
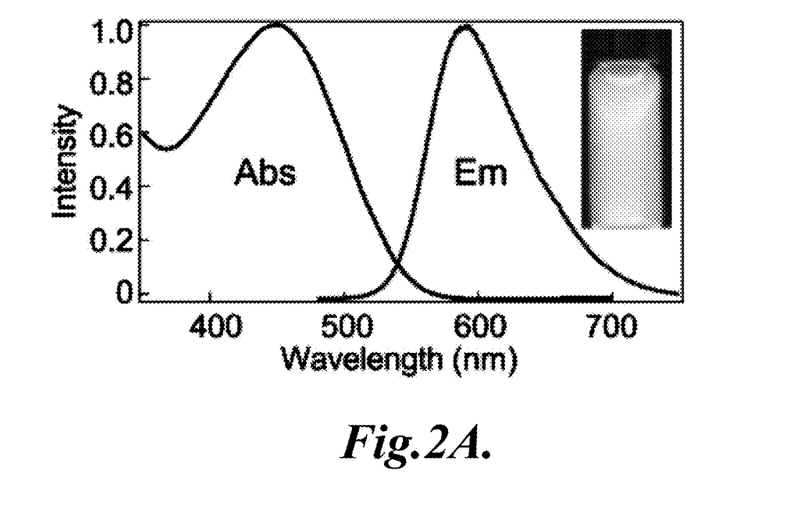
FIGS. 2A-2E. (2A) Absorption and emission of CN-PPV dot, inset shows the fluorescence image of a Pdot solution under a UV lamp. (2B) Fluorescence decay lifetime (1.5 ns) of CN-PPV dots measured by a time-correlated single-photon counting instrument (TCSPC). Fluorescence intensity distributions of (2C) unlabeled MCF-7 cells, (2D) MCF-7 cells incubated with Pdot-streptavidin (Pdot-SA) in the absence of antibody (Ab), and (2E) MCF-7 cells labeled with Pdot-SA and the biotinylated primary antibody against EpCAM. In the flow-cytometry experiment, a 488 nm laser excitation and a 582/42 nm band pass filter was used.
Figure 2B:
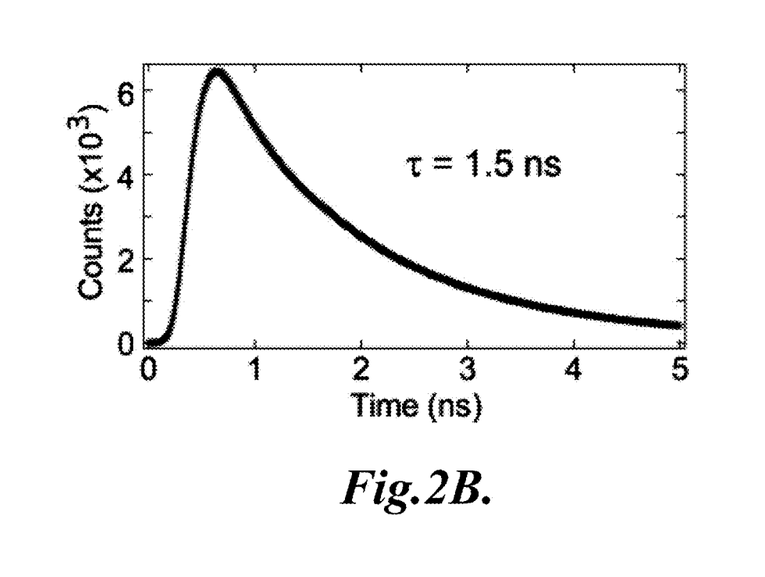

Importantly, the brightness of the CN-PPV dot's fluorescence remained unchanged after carboxyl surface modification and streptavidin bioconjugation. Both the bare Pdots and surface-modified Pdots showed a similar quantum yield of ~60% with a peak absorption cross section as large as $2.3 \times 10^{-13}$ cm$^2$ for a 10 nm Pdot. This combination of high quantum yield and high cross section makes CN-PPV Pdots brighter by several orders of magnitude than conventional organic dyes, such as Alexa. FIG. 2A shows the absorption and emission spectra of the CN-PPV Pdots. This Pdot can be conveniently excited by the 488 nm line of a blue laser, matching the CN-PPV Pdot well with most instruments currently available for biological imaging or flow cytometry. Using a time-correlated single-photon counting instrument (TCSPC) (FIG. 2B), we determined CN-PPV dots have a fluorescence lifetime of ~1.5 ns, which is about 2-3 times shorter than most dyes that emit in the visible range. The CN-PPV Pdots also possessed high photostability; their fluorescence lasted for several minutes under continuous exposure (power at sample stage was ~5 μW) of the 488 nm laser of the confocal microscope (Zeiss LSM 510).

Figure 2C:
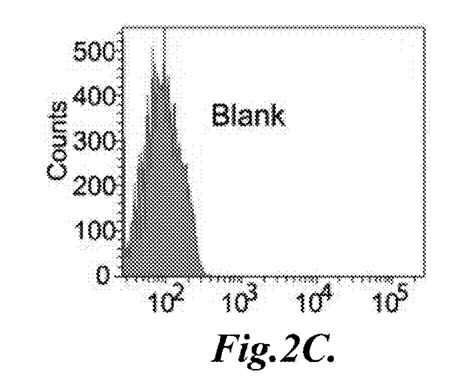
Figure 2D:
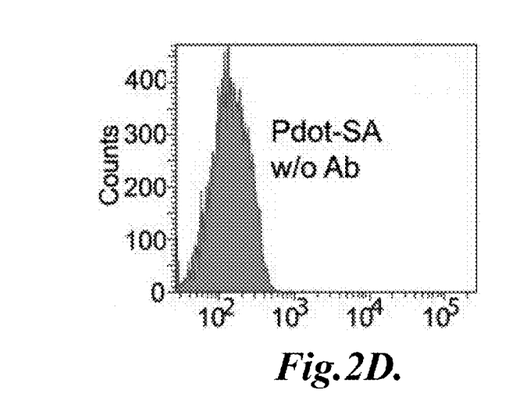
Figure 2E:
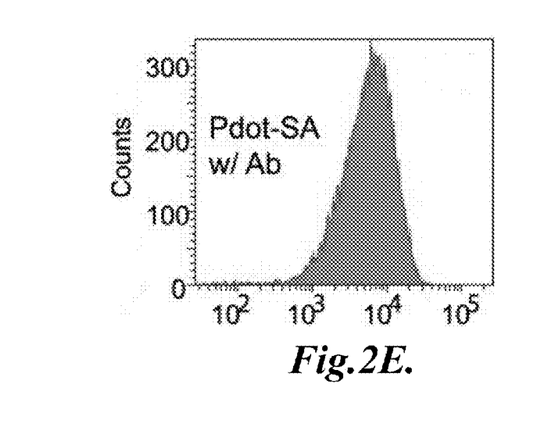

We conducted flow cytometry to examine the specific binding of the CN-PPV bioconjugates. In this experiment, the Pdot-streptavidin probes and biotinylated primary anti-EpCAM antibody were used to label the cell-surface EpCAM receptors on MCF-7 cells (ESI). The fluorescence intensity of MCF-7 cells incubated with only Pdot-streptavidin (no antibody; FIG. 2D) was similar to that of blank MCF-7 cells (FIG. 2C), suggesting that nonspecific binding was absent or extremely low for CN-PPV Pdot probes. The positive labeling with Pdot-streptavidin and biotinylated primary antibody (FIG. 2E) exhibited strong fluorescence compared to the two control samples, indicating the high brightness of CN-PPV probes and the high specificity they have for their targets.

Figure 3A:
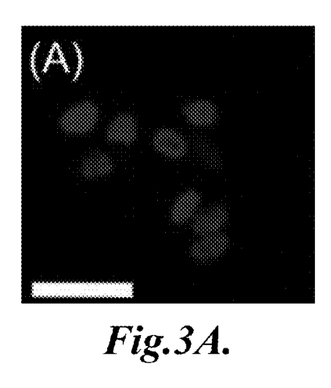
FIGS. 3A-3G. Two-color confocal fluorescence microscopy images of microtubules in HeLa cells labeled with Pdot-streptavidin. One channel was for the nucleus stain while the second channel showed emission from CN-PPV Pdots. For (3A-3D), cells were incubated with Pdot-streptavidin but in the absence of biotinylated primary antibody, clearly showing the absence of non-specific binding. (3A) Image of nucleus; (3B) Image of microtubules; (3C) bright-field image of cells; (3D) two-color image obtained by merging panels (3A) and (3B). The scale bar in (3A) is 50 μm. (3E-G) are two-color images showing cells that were incubated with both Pdot-streptavidin and biotinylated anti-α-tubulin. The scale bars represent 50 μm, 10 μm and 10 μm for (3E), (3F), and (3G), respectively.
Figure 3B:
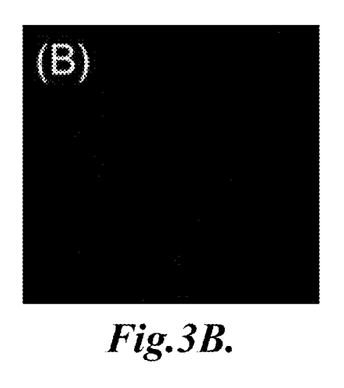
Figure 3C:
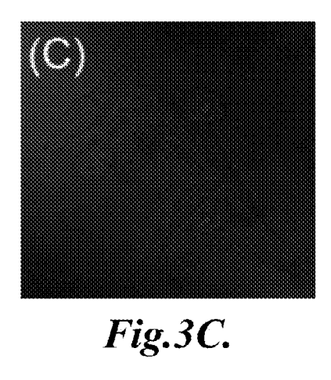
Figure 3D:
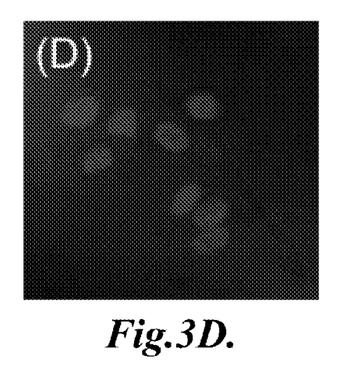
Figure 3E:
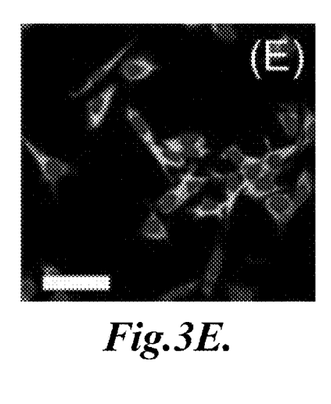
Figure 3F:
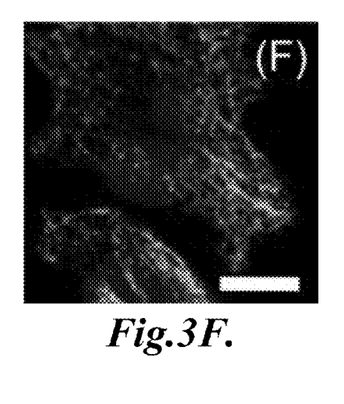
Figure 3G:
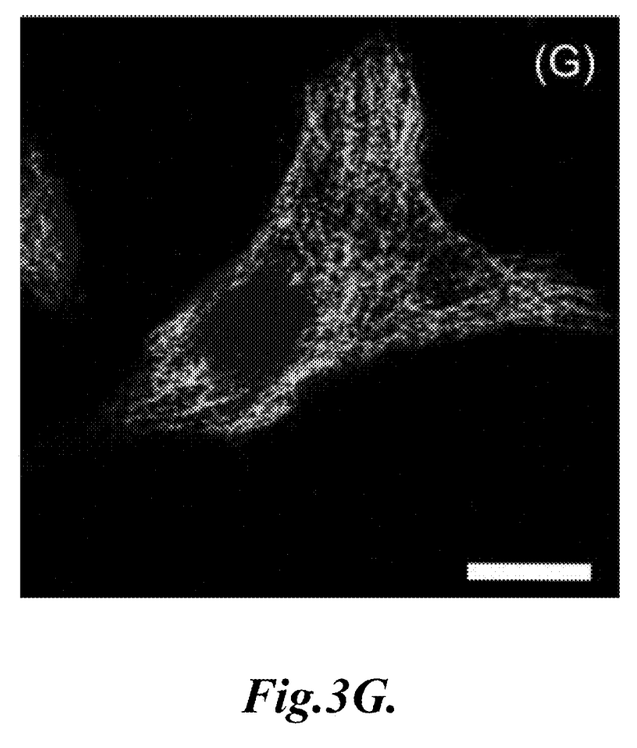

Finally, we carried out subcellular microtubule labeling in HeLa cells. Hela cells were fixed with 4% paraformaldehyde in phosphate buffered saline (PBS) and then permeabilized with 0.25% Triton-X 100/PBS solution. Biotinylated monoclonal anti-α-tubulin antibody and CN-PPV-streptavidin probes were then added to label microtubule structures in HeLa cells (ESI). The HeLa cells incubated with Pdots in the presence or absence of biotinylated antibody were imaged by confocal microcopy (ESI). FIGS. 3A-D shows the confocal images of HeLa cells incubated with Pdot-streptavidin without antibody where fluorescence wasn't detected (FIG. 3B). In contrast, FIGS. 3E-G show representative confocal images at different magnifications of cells incubated with both Pdot-streptavidin and biotinylated anti-α-tubulin; specific and extremely bright fluorescence was observed from the labeled microtubules. Individual tubular structures were clearly seen and were well-resolved in the images. Under the same labeling conditions, similarly high-quality images of subcellular structures were not observed in our previous report when we used PFBT-streptavidin probes. The primary reason for this difference may be that the compact and small size of CN-PPV Pdot conjugates exhibited ultra low nonspecific binding in the subcellular environment compared to the larger PFBT probes. This feature of low nonspecific binding is advantageous for most biological applications, such as imaging cellular and subcellular targets.

In conclusion, we report a new Pdot that is compact and extremely bright. It spectrally complements existing Pdots because there currently aren't any Pdots that emit in the orange wavelength range with high brightness. The CN-PPV Pdots didn't show noticeable nonspecific binding during subcellular imaging. The small particle size, high brightness, and the ability to highly specifically target subcellular structures make the CN-PPV dots promising probes for biological imaging and bioanalytical applications.

Materials and Methods

Functionalization of Semiconducting Polymer Dots.

The fluorescent semiconducting polymer Poly[2-methoxy-5-(2-ethylhexyloxy)-1,4-(1-cyanovinylene-1,4-phenylene)] (CN-PPV, MW 15,000, polydispersity 5.9) was purchased from ADS Dyes, Inc. (Quebec, Canada). The copolymer poly(styrene-co-maleic anhydride) (PSMA, cumene terminated, average Mn ~1,700, styrene content 68%) was purchased from Sigma-Aldrich (St. Louis, Mo., USA). All other reagents for nanoparticle preparation were purchased from Sigma-Aldrich (St. Louis, Mo., USA), and all experiments were performed at room temperature unless indicated otherwise. Functionalized Pdots in aqueous solution were prepared by using a modified nanoprecipitation method. In a typical preparation, the fluorescent semiconducting polymer CN-PPV was first dissolved in tetrahydrofuran (THF) to make a 1 mg/mL stock solution. The copolymer PSMA was also dissolved in THF and mixed with a diluted solution of CN-PPV to produce a solution mixture with a CN-PPV concentration of 50 μg/mL and a PSMA concentration of 10 μg/mL. The mixture was sonicated to form a homogeneous solution. A 5 mL quantity of the solution mixture was quickly added to 10 mL of MilliQ water in a bath sonicator. The THF was removed by nitrogen stripping, and the solution concentrated to 5 mL on a 90° C. hotplate followed by filtration through a 0.2 micron filter. During nanoparticle formation, the maleic anhydride units of PSMA molecules were hydrolyzed in the aqueous environment, generating carboxyl groups on Pdots. The Pdot dispersions were clear and stable for months without signs of aggregation.

Biomolecular Conjugation to Functionalized Pdots.

Streptavidin was purchased from Invitrogen (Eugene, Oreg., USA). In this paper, we performed bioconjugation by utilizing the EDC-catalyzed reaction between carboxyl groups on Pdots and amine groups on streptavidin. In a typical bioconjugation reaction, 100 μL of polyethylene glycol (5% w/v PEG, MW 3350) and 100 μL of concentrated HEPES buffer (1 M) were added to 5 mL of functionalized Pdot solution (50 μg/mL in MilliQ water), resulting in a Pdot solution in 20 mM HEPES buffer with a pH of 7.3. Then, 200 μL of streptavidin (1 mg/mL) was added to the solution and mixed well on a vortex. Finally, 100 μL of freshly-prepared EDC solution (5 mg/mL in MilliQ water) was added to the solution. The mixture was left on a rotary shaker for 4 hours at room temperature. The resulting Pdot-streptavidin bioconjugates were separated from free streptavidin by gel filtration using Sephacryl HR-300 gel media.

Characterization of Functionalized Pdots.

The particle size of Pdots in bulk solution was characterized by dynamic light scattering (Malvern Zetasizer NanoS). For the TEM measurements, one drop of the Pdot dispersion was placed on a carbon-coated copper grid. After evaporation of the water, the nanoparticles were imaged with a transmission electron microscope (FEI Tecnai F20). UV-Vis absorption spectra were recorded from the Pdots in 1 cm quartz cuvettes with a DU 720 scanning spectrophotometer (Beckman Coulter, Inc., CA USA). Fluorescence spectra were obtained using a commercial Fluorolog-3 fluorometer (HORIBA Jobin Yvon, NJ USA). Agarose gel electrophoresis of the functionalized Pdots was carried out using a Mupid®-exU submarine electrophoresis system. Pdots (in 30% glycerol) were loaded onto a 0.7% agarose gel containing 0.1% PEG. The Pdot-loaded gel was run for 20 min at 135 V in tris-borate-EDTA (TBE) buffer, and then imaged on Kodak image station 440CF system.

Cellular and Subcellular Labeling.

The MCF-7 cells were labeled for flow cytometry with primary anti-EpCAM antibody (0.5 mg/mL, Biolegend) and biotin secondary anti-mouse IgG (0.5 mg/mL, Biolegend). Other reagents were the labeling buffer (1×PBS containing 1% BSA and 2 mM EDTA) and BlockAid™ blocking buffer (Invitrogen). A million MCF-7 cells were dispersed in 100 μL of labeling buffer in a 5 mL round-bottom tube. 1 μL of primary anti-EpCAM antibody (0.5 mg/mL) was added to the cell suspension. The cell suspension was left on a rotary shaker for 30 minutes. Then 4 mL of labeling buffer was added to the tube. The cells were centrifuged down to the tube bottom to wash off free primary antibody. The cells were dispersed in 100 μL of labeling buffer. An aliquot of 1 μL of biotin secondary anti-mouse IgG (0.5 mg/mL, Biolegend) was added, and the cell suspension was left on a rotary shaker for 30 minutes. Next, 5 μL of Pdot-streptavidin conjugates (~200 nM) was well-dispersed into 200 μL BlockAid™ blocking buffer (Invitrogen). The final Pdot concentration for cell labeling was ~5 nM. An aliquot of 4 mL of labeling buffer was added to the cell tube after 30 minutes of secondary antibody incubation. The cells were pelleted by centrifugation and then resuspended with 200 μL of Pdot-steptavidin in BlockAid™ buffer. The cell suspension was left on rotary shaker for 30 minutes. An aliquot of 4 mL of labeling buffer was added to the cell tube and the cells were pelleted by centrifugation to wash off free Pdot-streptavidin conjugates. The step was repeated twice, and the resultant cells were run through the flow cytometer.

For subcellular microtubule-labeling experiment, Block-Aid™ blocking buffer was purchased from Invitrogen (Eugene, Oreg., USA). Ten thousands of HeLa cells were plated on a 22×22 mm glass coverslip and cultured until the density reach 60-70% confluence. The cells were fixed with 4% paraformaldehyde for 15 minutes, permeabilized with 0.25% Triton-X 100 in PBS for 15 minutes, and blocked in BlockAid™ blocking buffer for 30 minutes. The fixed and blocked HeLa cells were incubated sequentially with 5 μg/mL biotinylated monoclonal anti-α-tubulin antibody (Biolegend, San Diego, Calif., USA) for 60 minutes, and 5 nM CN-PPV-streptavidin conjugates for 30 minutes. The Pdot-tagged cells were then counterstained with Hoechst 34580 and imaged immediately on a fluorescence confocal microscope (Zeiss LSM 510).

Subcellular Imaging.

The fluorescence images of HeLa cells were acquired with a fluorescence confocal microscope (Zeiss LSM 510). Blue channel, green channel emission and bright field image were simultaneously obtained. The blue channel was excited by 405 nm diode laser, while the green channel was excited by a 488 nm diode laser. A Carl Zeiss 63×("C-Apochromat" 63×/1.2 oil Corr) and a Carl Zeiss 100×("C-Apochromat" 100×/1.45 oil Corr) objective lens were utilized for imaging and spectral data acquisition. The laser was focused to a spot size of ~5 μm, and the laser power in the sample stage was about 5 μW for 488 nm diode laser.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle consisting essentially of:
   poly[2-methoxy-5-(2-ethylhexyloxy)-1,4-(1-cyanovinylene-1,4-phenylene)];
   a copolymer; and
   a binding moiety covalently attached to the copolymer, wherein the binding moiety is a protein, and wherein the nanoparticle has a hydrodynamic diameter of 1-30 nm and a quantum yield of about 60%.

2. The nanoparticle of claim 1, wherein the hydrodynamic diameter is 20 nm or less.

3. The nanoparticle of claim 1, having a fluorescence emission peak in the range of about 590 nm to about 620 nm.

4. The nanoparticle of claim 1, wherein the nanoparticle is formed using nanoprecipitation.

5. The nanoparticle of claim 1, wherein the copolymer is poly(styrene-co-maleic anhydride).

6. The nanoparticle of claim 1, wherein the binding moiety is positioned at the surface of the nanoparticle.

* * * * *